United States Patent [19]

Morrow et al.

[11] Patent Number: 5,147,791
[45] Date of Patent: Sep. 15, 1992

[54] ENZYME CATALYZED SYNTHESIS OF POLYESTERS

[75] Inventors: Cary J. Morrow; Joe S. Wallace, both of Albuquerque, N. Mex.

[73] Assignee: University of New Mexico, Albuquerque, N. Mex.

[21] Appl. No.: 759,971

[22] Filed: Sep. 17, 1991

Related U.S. Application Data

[63] Continuation of Ser. No. 333,675, Apr. 6, 1989, abandoned.

[51] Int. Cl.$^5$ .......................... C12P 17/02; C12P 7/62
[52] U.S. Cl. .................... 435/123; 435/134; 435/135
[58] Field of Search ............... 435/280, 123, 134, 135

[56] References Cited

U.S. PATENT DOCUMENTS

| | | | |
|---|---|---|---|
| 3,072,538 | 1/1963 | Baptist | 195/101 |
| 3,225,766 | 12/1965 | Baptist et al. | 128/335.5 |
| 4,138,291 | 2/1979 | Lafferty | 195/47 |
| 4,140,741 | 2/1979 | Lafferty et al. | 264/184 |
| 4,451,565 | 5/1984 | Gatfield et al. | 435/117 |
| 4,472,503 | 9/1984 | Matsuo et al. | 435/176 |
| 4,477,654 | 10/1984 | Holmes et al. | 528/361 |
| 4,565,782 | 1/1986 | Bewick | 435/122 |
| 4,568,641 | 2/1986 | Bewick | 435/122 |
| 4,686,307 | 8/1987 | Farbood et al. | 560/205 |
| 4,705,604 | 11/1987 | Vanlautem et al. | 203/67 |
| 4,719,178 | 1/1988 | Macrae et al. | 435/135 |
| 4,732,853 | 3/1988 | Whitesides et al. | 435/123 |
| 4,735,900 | 4/1988 | Urata et al. | 435/134 |

OTHER PUBLICATIONS

Matsumura et al., CA 105:98043a (1986).
Okumura et al., *Agric. Biol. Chem.*, 48, 2805 (1984).
Ajima et al., *Biotechnology Lett.*, 7, 303 (1985).
Kitazume et al., *Chem. Express*, 3, 135 (1988).
Margolin et al., *Tetrahedron Letters*, 28 1607 (1987).

*Primary Examiner*—Carolyn Elmore
*Attorney, Agent, or Firm*—Lowe, Price, LeBlanc & Becker

[57] ABSTRACT

A method for synthesizing a polyester comprises reacting a diester and a dialcohol at approximately ambient temperature in the presence of an enzyme catalyst, preferably a lipase comprising porcine pancreatic lipase. The method is particularly adapted for enantioselective polymerization resulting in an optically active polyester. The polyesters preferably exhibit a weight average molecular weight, Mw, as measured by gel permeation chromatography of at least about 3000.

19 Claims, No Drawings

5,147,791

ENZYME CATALYZED SYNTHESIS OF POLYESTERS

This application is a continuation of application Ser. No. 07/333,675 filed Apr. 6, 1989, now abandoned.

FIELD OF THE INVENTION

The present invention relates to a method for the enzyme catalyzed synthesis of polyesters by the reaction of a diester and a dialcohol. The method according to the present invention is particularly adapted for enantioselectively polymerizing a diester and a diol to form an optically active polyester.

BACKGROUND OF THE INVENTION

During the past several years, it has been demonstrated that enzyme-catalyzed reactions in anhydrous, low polarity organic solvents represent a valuable addition to organic chemistry. Various reactions employing enzymes as catalysts have been disclosed, including esterifications, transesterifications, aminolyses and lactonizations. Except for naturally occurring polyesters such as poly(beta-hydroxybutyrate), there appears to have been limited previous effort to prepare polyesters using enzymes as catalysts. See, for example, Okumura et al, *Agric. Biol. Chem.*, 48, 2805 (1984); Ajima et al, *Biotechnology Lett.*, 7, 303 (1985); Matsumura et al, *Makromol. Chem., Rapid Commun.*, 7, 369 (1986); Kitazume et al, *Chem. Express*, 3, 135 (1988); and Margolin et al, *Tetrahedron Letters*, 28, 1607 (1987). For example, Okumura et al describe the *Aspergillus niger* lipase catalyzed oligomerization of 1,2-ethanediol and 1,3-propanediol with the diacids from 1,6-hexanedioic acid through 1,14-tetradecanedioic acid using either excess diol or excess diol with a small amount of water added as the solvent system. The only products examined in detail proved to be a "trimer", a "pentamer" and a "heptamer" of the forms AA-BB-AA, AA-BB-AA-BB-AA, and AA-BB-AA-BB-AA-BB-AA, respectively, which formed from 1,3-propanediol (AA) and 1,13-tridecanedioic acid (BB) in a ratio of 1:8:4.5 after 24 hours. The words "dimer", "trimer", etc. have been placed in quotes to reflect that they are being used to indicate the total number of monomer units in the oligomer rather than the number of repeat units. Thus, the "dimer" is really one repeat unit, the "trimer" is really 1.5 repeat units, the "pentamer" is really 2.5 repeat units, etc. Separation of the higher oligomers from the reaction mixture seemed to limit the degree of polymerization possible, but, at the same time, protected the oligomers from enzymatic hydrolysis or transesterification by the large excess of diol present. Apparently the "heptamer" is either too insoluble to have a favorable rate of conversion to higher oligomers or its rate for acylating the enzyme at other than a terminal ester is rapid, and it is converted back to lower oligomers.

Ajima et al described the first attempted enzyme-catalyzed polymerization of an A-B type monomer, 10-hydroxydecanoic acid. The reaction was performed in benzene using a poly(ethyleneglycol) solubilized lipoprotein lipase from *Pseudomonas fluorescens*. The product was found to have a longer retention on gel permeation chromatography (GPC) than did the monomer suggesting a structure having a smaller molecular volume. In the absence of data to the contrary, it seems likely that the product was a lactone or, possibly, a bislactone (dilide) rather than the proposed oligomeric material.

Matsumura et al also described attempted polymerizations of ω-hydroxycarboxylic acids in water and in organic solvents using lipases from *Candida rugosa* and *Chromobacterium viscosum* as the catalysts. The substrates chosen were the primary alcohols 12-hydroxydodecanoic acid and 16-hydroxyhexadecanoic acid and the secondary alcohols 12-hydroxyhexadecanoic acid and 12-hydroxy-cis-9-octadecenoic acid. While most of the substrate was consumed, the products, even with primary alcohols, were principally trimers and tetramers.

Kitazume et al described a second polymerization of an A-B monomer. A prochiral fluorine-substituted diester was enantioselectively hydrolyzed to the corresponding half-ester with lipase from the yeast *Candida cylindracea*. The resulting carboxylic acid was coupled nonenzymatically with the amine in a t-butyldimethylsilyloxy aniline or the unprotected amine in N-acetyl-1,4-benzenediamine to provide, after deprotection and hydrolysis of the remaining ester, an hydroxy acid or an amino acid A-B monomer. The monomer was polymerized using a modified cellulase from *Trichoderma viride* in benzene, hexane, or $Cl_2CFCF_2Cl$. Molecular weights (Mw) as high as 18,500 daltons and low polydispersities (1.09–1.51) were found for the polyester and polyamide products. However, the source of this example's success, in view of the very limited success of the related reactions just described, is unclear.

Margolin et al have described the stereoselective reaction of bis(2-chloroethyl)($\pm$)-2,5-dibromoadipate with 1,6-hexanediol, the reaction of bis(2,2,2-trichloroethyl)($\pm$)-3-methyladipate with 1,6-hexanediol, and the reaction of bis(2-chloroethyl) adipate with ($\pm$)-2,4-pentanediol in toluene using commercially available lipases as catalysts. In each case, the reaction was allowed to continue for an extended period and provided, principally, a mixture of a "trimer" and a "pentamer" of the forms AA-BB-AA and AA-BB-AA-BB-AA where AA represents the diol and BB represents the diacid moiety of the oligomer.

SUMMARY OF THE INVENTION

It is an object of the present invention to provide a method for synthesizing polyesters, which method employs an enzyme catalyst. It is a further object of the invention to provide such a method wherein the resulting polyester includes a significant number of repeating units. It is a further object of the invention to provide a method for enantioselectively polymerizing diester and diol reactants to form optically active polyesters of high stereochemical purity.

These and additional objects are provided by the method according to the present invention which comprises reacting a diester and a dialcohol in a low to intermediate polarity organic solvent at approximately ambient temperature in the presence of an enzyme catalyst, preferably a lipase catalyst. The present inventors have discovered that such a reaction may be employed to enantioselectively polymerize a diester and a diol to form an optically active polyester. The resulting polymers include a significant number of repeating units and may exhibit a weight average molecular weight, Mw, as measured by gel permeation chromatography of at least 3000. Additionally, because the reaction of the present method is effected at ambient temperature, suitable reactants may be employed to introduce reactive functionality, for example epoxy groups, into the resulting polymer. Thus, the present method may be employed to introduce into the polymers reactive functionality which generally will probably not survive the usual conditions for polyester formation.

These and additional objects and advantages will be more apparent in view of the following detailed description.

DETAILED DESCRIPTION

According to the method of the present invention, polyesters are synthesized by the reaction of a diester and a dialcohol. The reaction may be effected at approximately ambient temperature and in the presence of an enzyme catalyst. Approximately ambient temperature means ambient temperature and slightly above or below ambient temperature, for example 10° C. above or below ambient temperature. Additionally, in many cases the reaction may be effected at higher temperatures, for example up to 100° C., at which improved reaction rates are attained. In one embodiment in which the diester is of racemic character, the diester and diol are employed in a molar ratio of about 2:1. In another embodiment in which the diester is not of racemic character, the diester and diol are employed in an equimolar ratio. Preferred enzyme catalysts comprise hydrolases. Particularly preferred enzyme catalysts comprise lipases. Particularly successful results have been achieved by the use of an enzyme catalyst comprising porcine pancreatic lipase (PPL).

The reaction employed in the method of the present invention is preferably conducted in the presence of an organic solvent. Suitable organic solvents comprise anhydrous organic solvents of low to intermediate polarity. For example, suitable solvents include hexane, diethyl ether, diisopropyl ether, dipropyl ether, tetrahydrofuran, benzene, 1,1,2-trichlorotrifluoromethane, chloroform, o-dichlorobenzene, and mixtures of methylene chloride with hexane or ether. Successful results have been achieved when the organic solvent was selected from diethyl ether, diisopropyl ether, benzene, tetrahydrofuran, and mixtures of methylene chloride with hexane or ether.

The polyesters which are formed according to the present method include a repeating unit of the general formula [AA-BB] wherein AA represents a unit resulting from the diester reactant and BB represents a unit resulting from the diol reactant. In one embodiment of the present method, the diester employed in the reaction comprises a bis-substituted alkanedioate of the following formula I:

$$\underset{ROC(CH_2)_nCOR}{\overset{O}{\underset{\|}{\phantom{X}}}\overset{O}{\underset{\|}{\phantom{X}}}} \quad (I)$$

wherein n is an integer of from 2 to about 10, and R is an organic leaving group which forms a byproduct during the polymerization reaction. Preferred R groups include alkyl groups; halogen-substituted alkyl groups, for example —CH$_2$CH$_2$Cl, —CH$_2$CH$_2$F, —CH$_2$CCl$_3$, —CH$_2$CF$_3$; alkenyl groups, for example vinyl (—CH═CH$_2$), 2-propenyl (—C(CH$_3$)═CH$_2$); aryl, for example phenyl (—Ar); mono- or poly-substituted aryl, for example -Ar-halogen, —Ar—NO$_2$, —Ar-C≡N; aroyl, for example benzoyl (—C(O)Ar), and the like. It is believed that the nature of the leaving groups effects the molecular weight of the resulting polymer. As is demonstrated in the Examples, particularly successful results have been achieved when the diester comprises a glutarate (n=3) or an adipate (n=4), and when R is —CH$_2$CCl$_3$.

A related diester which is particularly preferred for use in the method of the present invention comprises bis(2,2,2-trichloroethyl)(±)-3,4-epoxyadipate of the formula II:

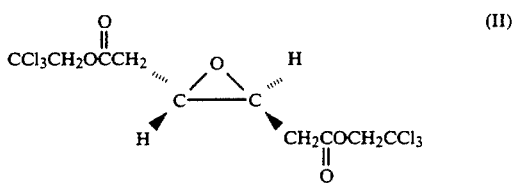

Alternatively, the diester may comprise bis(R)(±)-3,4-epoxyadipate in which R is as defined above. Preferred R groups for use in this embodiment include phenyl, 4-nitrophenyl, 4-chlorophenyl, 4-fluorophenyl, 4-bromophenyl and 2,4-dichlorophenyl.

In one embodiment, diols for use in forming the polyesters according to the present method are of the formula HO—X—OH wherein X comprises a hydrocarbon group containing from about 4 to about 15 carbon atoms. As is demonstrated in the Examples, particularly successful results have been obtained when the diol is of the formula HOCH$_2$—Z—CH$_2$OH wherein Z represents a hydrocarbon group containing from about 2 to about 10 carbon atoms. Examples of diols suitable for use in the present method include normal alkane diols such as 1,4-butanediol, 1,5-pentanediol, 1,6-hexanediol, 1,8-octanediol, 1,4-cyclohexanedimethanol, 1,4-benzenedimethanol, 1,4cyclohexanediol, hydroquinone, bisphenol A, 2,2'-biphenol, 4,4'-biphenol, 2,4-pentanediol, threitol, 2,3-epoxy-1,4-butanediol and 1,1'-(1,4-benzene)diethanol. Preferred diols comprise 1,4-butanediol, 1,6-hexanediol, 1,12-dodecanediol and 1,4-cyclohexanedimethanol.

In one preferred embodiment of the present method, the diester comprises a bis(2,2,2-trichloroethyl) alkanedioate or bis(2,2,2-trifluoroethyl) alkanedioate and the diol is of the formula HOCH$_2$—Z—CH$_2$OH, and the reaction according to the present invention proceeds as follows, in the case of the trichloroethyl substituted reactant:

$$CCl_3CH_2OC(CH_2)_nCOCH_2CCl_3 + HOCH_2-Z-CH_2OH$$

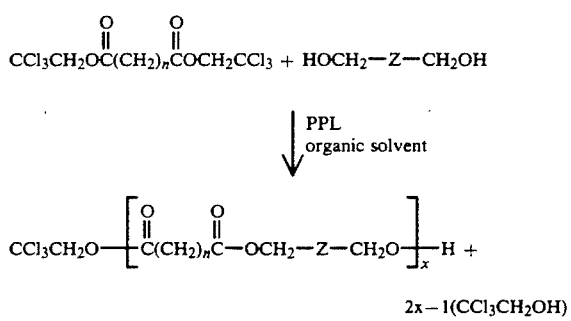

Similarly, in another preferred embodiment, the diester comprises bis(2,2,2-trichloroethyl)(±)-3,4-epoxyadipate and the diol comprises 1,4-butanediol, and the reaction according to the present method proceeds as follows:

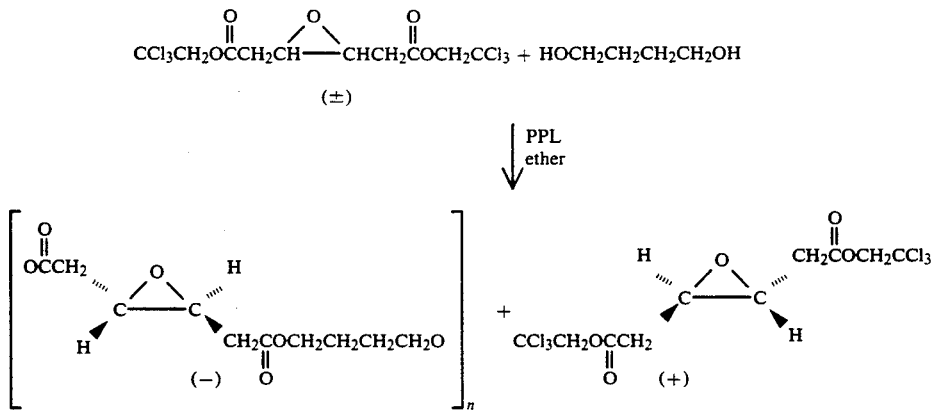

Thus, this reaction gives an optically active polyester of high stereoregularity (estimated to contain at least 96% of one enantiomer of the racemic starting monomer) while leaving the second enantiomer unchanged (estimated enantiomeric excess of at least 95%). Moreover, the polymer retains the reactive epoxy functional group which may subsequently be used to effect crosslinking of the polymer.

The method according to the present invention will be more fully understood in view of the following examples.

EXAMPLE 1

This example demonstrates the synthesis of bis(2,2,2-trichloroethyl)($\pm$)-3,4-epoxyadipate employed in the diester-diol reaction of the present invention. This synthesis was performed according to the general method of Dahill et al, *Org. Chem.*, 35, 251 (1970). To a 300 mL three-necked round bottom flask equipped with a magnetic stirrer and nitrogen inlet was added 8.50 g (20.9 mmol) of bis(2,2,2-trichloroethyl) trans-3-hexenedioate, and 50 mL of anhydrous dichloromethane. To the resulting solution was added 9.03 g (52.3 mmol) of 85% m-chloroperoxybenzoic acid (Aldrich Chemical Co., #C6,270-0) dissolved in 100 mL of dichloromethane. The mixture was stirred in a nitrogen atmosphere at ambient temperature for three days at which time gas chromatographic analysis showed the starting material to have been consumed and during which time a voluminous precipitate formed. The excess m-chloroperoxybenzoic acid was destroyed by addition of excess saturated aqueous sodium sulfite solution. After five minutes, a negative test was obtained with starch iodide test paper. The insoluble m-chlorobenzoic acid was removed by filtration and the filtrate was washed successively with 100 mL of the saturated solution of sodium sulfite, 100 mL of saturated aqueous sodium bicarbonate solution and 100 mL of saturated brine. After drying over magnesium sulfate, the dichloromethane was evaporated to give 7.75 g (91% yield) of a colorless oil that crystallized on standing at 0° C. Analytically pure material was obtained by chromatography on silica gel, eluting with a 1:1 hexane/dichloromethane mixture. The material exhibited the following characteristics: m.p. 55.-56° C.; $^1$H NMR (CDCl$_3$): 2.78 (multiplet, 4H, —OC(O)CH$_2$—); 3.22 (triplet, 2H, —CH(O)(C)); 4.78 (singlet, 4H, —OCH$_2$CCl$_3$). *Anal. Calc'd.* for C$_{10}$H$_{10}$Cl$_6$O$_5$:C, 28.40; H, 2.38. Found: C, 28.49; H, 2.39.

EXAMPLE 2

This example demonstrates the polymerization of bis(2,2,2-trichloroethyl)($\pm$)-3,4-epoxyadipate with 1,4-butanediol according to two methods, A and B.

The diester monomer produced according to Example 1 was recrystallized twice from 20:1 hexane/dichloromethane solution then carefully dried in vacuum at 40° C. for 48 hours. The 1,4-butanediol (Aldrich Chemical Co., #24,055-9 Gold Label) was purchased anhydrous and was greater than 99% pure. A crude preparation of porcine pancreatic lipase (35% protein, activity =35-70 units per mg of protein using triacetin, Sigma Chemical Co., #L 3126) was purchased and then dried in vacuum over phosphorus pentoxide for three days.

Method A 8.7170 mmol of the bis(2,2,2-trichloroethyl)($\pm$)-3,4-epoxyadipate and 4.3586 mmol of 1,4-butanediol were dissolved in 18 mL of anhydrous diethyl ether, the 1,4-butanediol being only partially soluble. To this mixture was added 2.5 g of the porcine pancreatic lipase preparation and the resulting slurry was stirred mechanically in a dry nitrogen atmosphere while the disappearance of 1,4-butanediol and the appearance of 2,2,2-trichloroethanol was monitored by gas chromatography. After six hours the 1,4-butanediol had dissolved completely and gas chromatography (GC) analysis showed it to have been consumed completely. After stirring for 3.5 days at ambient temperature, the enzyme was removed by suction filtration and washed with dichloromethane. The washes were combined with the filtrate and the solvents removed by evaporation to provide a viscous oil which was stirred for one hour with diethyl ether. The ether phase was poured off and the washing process repeated. The ether washes were combined and concentrated to provide 1.71 g (93% yield) of a colorless oil which was shown by GC, thin layer chromatography and $^1$H NMR to be principally (greater than 95%) unchanged diester. However, a methanol solution showed a specific rotation $[\alpha]_D + 12.3°$. The ether insoluble oil was dried in vacuum to provide 0.68 g (73% yield) of an extremely viscous, colorless oil which was shown by $^1$H NMR and gel permeation chromatography to be poly(1,4-butanediol 3,4-epoxyadipate) having a number average molecular weight, M$_N$, of 5,300 daltons and a weight average molecular weight, M$_w$, of 7,900 daltons. A CHCl$_3$ solution gave $[\alpha]_D = -13.4°$ $^1$H NMR (CDCl$_3$):

1.70 (multiplet, 4H, CH$_2$—); 2.59 (two doublet of doublets, 4H, —OC(O)CH$_2$—); 3.12 triplet, 2H, —CH(O)(C)); 4.13 (multiplet, 4H, —CH$_2$OC(O)—).

The unchanged (+) enantiomer of the diester was shown to have an enantiomeric excess of greater than 95% by proton NMR in the presence of the chiral shift reagent Eu(hfc)$_3$. The stereochemical purity of the (−)polymer was estimated at greater than 96% by consideration of the amount of the slower reacting enantiomer that could have been incorporated and still attain the observed degree of polymerization (25) when the starting ratio of racemic diester to diol was 2:1. Direct determination of the stereochemical purity of the polymer using Eu(hfc)$_3$ was unsuccessful.

Method B 15.3600 mmol of bis(2,2,2-trichloroethyl)(±)-3,4-epoxyadipate and 7.6790 mmol of 1,4-butanediol were dissolved in 35 mL of anhydrous diethyl ether. To this mixture was added 4.5 g of the porcine pancreatic lipase. The resulting slurry was stirred magnetically in a dry nitrogen atmosphere for about 1.5 days, after which time a phase separation between the diethyl ether and an enzyme/polymer phase was observed. The mobile ether phase was removed with a pipet and 30 mL of fresh, anhydrous ether was added. The resulting mixture was stirred for four hours to extract the unreacted enantiomer of the monomer and the trichloroethanol product from the enzyme/polymer phase. The ether phase was again removed and replaced with 20 mL of a 3:1 (v/v) mixture of dichloromethane and ether. The viscous polymer dissolved in this new solvent and the resulting slurry was stirred at ambient temperature in a nitrogen atmosphere for an additional 3.5 days. The trichloroethanol in the residual oil was removed by Kugelrohr distillation at 55° C. (0.5 mm Hg) to leave 3.19 g (98% yield) of the unreacted diester enantiomer as a colorless oil. The Kugelrohr distillation apparatus was supplied by Aldrich Chemical Co. as catalog #Z10,046-3. The oil crystallized after further purification by flash chromatography on silica gel, eluting with dichloromethane. When the polymerization was complete, the dichloromethane/ether solution was worked up as described for Method A above to give 1.57 g (96% yield) of an extremely viscous oil.

The molecular weight determinations were performed as follows throughout the present examples:

END GROUP ANALYSIS

Polymer end groups were detected and quantitated by $^1$H NMR spectrometry. In general, the area of the methylene proton absorption for the unreacted trichloroethyl ester groups and the area of the methylene proton absorption for groups adjacent to unesterified alcohols were added together and assigned a value of four protons. This area was then divided into the area of the absorption assigned to the esterified methylenes of the butanediol moiety which accounts for four protons per repeat unit. This quotient provides a DP for the polymer of 24.7. Multiplication by the repeat unit formula weight, 214 daltons, provides a M$_N$ of 5285. Two sources of error were considered: (1) hydrolysis of the trichloroethyl ester end groups which would make the estimate of M$_N$ high; and (2) the presence of a singlet at 3.62, perhaps assignable to end group hydroxyls, and a very small multiplet just upfield of the triplet at 3.65 ppm, perhaps arising from a trace of unreacted 1,4-butanediol, both of which would make the estimate of M$_N$ low. The former source was discounted because in other studies it has been shown that enzyme prepared as described herein does not cause significant hydrolysis of trichloroethyl ester end groups. The latter source is taken to limit the estimate to being a lower limit for DP until the cause of the extra peaks can be established with greater certainty.

GEL PERMEATION CHROMATOGRAPHIC (GPC) ANALYSIS

The GPC analyses were performed on a Zorbax PSM Bimodal column (DuPont Company) that had been calibrated with eight polystyrene standards ranging in molecular weight from 900 to 1,800,000 daltons. In all analyses, tetrahydrofuran was employed as the mobile phase. A commercial sample of poly(1,4-butanediol adipate) [Polysciences Inc., lot #51201] reported to have a Mw of 12,000 by light scattering gave a Mw of 14,000 under the analysis conditions.

EXAMPLE 3

This example demonstrates polymerization of bis(2,2,2-trichloroethyl) 1,6-hexanedioate with 1,4-butanediol. More particularly, recrystallized bis(2,2,2-trichloroethyl) 1,6-hexanedioate was further purified by molecular distillation (100° C. at 0.1 mm Hg). A mixture of 7.7918 mmol of the diester and 7.7918 mmol of 1,4-butanediol were mixed with 9 mL of anhydrous diethyl ether. To the resulting mixture was added 2.4 g of commercial porcine pancreatic lipase (Sigma Chemical Company, #L 3126) which had been dried in vacuum over phosphorus pentoxide for three days. The reaction was allowed to continue for five (5) days at ambient temperature in a nitrogen atmosphere. The partially dissolved diol disappeared as the reaction progressed. The rapid disappearance of the starting materials and the appearance of trichloroethanol was monitored by VPC and the reaction was allowed to continue four times as long as was required for complete disappearance of the starting materials. The reaction was terminated by addition of 10 mL of dichloromethane, after which the enzyme was filtered off and the solvent and trichloroethanol side product were removed by evaporation. The residue was redissolved in dichloromethane and the polymer precipitated by addition of methanol. The yield of the polymer was 84%. End group analysis by high field NMR provided a number average molecular weight (M$_N$) of 4,900 daltons. Analysis of the polymer by GPC provided an estimate of the weight average molecular weight (Mw) as 5,200 daltons.

EXAMPLES 4–15

Using the general procedure of Example 3 employed for the polymerization of bis(2,2,2-trichloroethyl 1,6-hexanedioate with 1,4-butandiol, additional polymers were prepared according to the method of the present invention according to the reaction:

$$CY_3CH_2OC(CH_2)_nCOCH_2CY_3 + HOCH_2-Z-CH_2OH$$

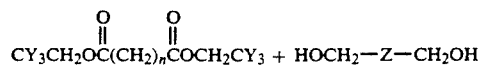

-continued

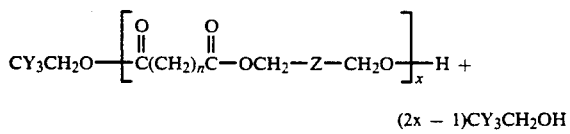

$$(2x - 1)CY_3CH_2OH$$

wherein Y is Cl or R. The reactants, solvents and reaction time employed are set forth in Table 1 together with the yield and molecular weight determinations of the resulting polymers.

TABLE 1

Enzymatic Synthesis of AA–BB Polymers by Transesterification

| Example | Diester n | Diester Y | Diol Z = | Solvent | Reaction Time (h) | Yield (%) | Mw (GPC) | Mn ($^1$H NMR) | Mw/Mn |
|---|---|---|---|---|---|---|---|---|---|
| 4 | 3 | Cl | (CH$_2$)$_2$ | ether | 122 | 89 | 11,800 | 8,200 | 1.44 |
| 5 | 3 | F | (CH$_2$)$_2$ | ether | 72 | 96 | 12,600 | 10,000 | 1.26 |
| 6 | 3 | F | (CH$_2$)$_2$ | ether/diisopropyl ether (2 steps) | 78 | 93 | 15,100 | 11,700* | 1.30 |
| 7 | 3 | Cl | c-C$_6$H$_{10}$ | THF | 74 | 92 | 14,900 | — | — |
| 8 | 4 | Cl | (CH$_2$)$_2$ | ether | 120 | 84 | 5,200 | 4,900 | 1.06 |
| 9 | 4 | Cl | (CH$_2$)$_2$ | ether | 135 | 89 | — | 5,600 | — |
| 10 | 4 | Cl | (CH$_2$)$_4$ | ether | 120 | 86 | — | 6,500 | — |
| 11 | 4 | Cl | (CH$_2$)$_{10}$ | THF | 92 | 87 | 5,900 | 2,100 | 2.80 |
| 12 | 4 | Cl | c-C$_6$H$_{10}$ | ether | 96 | 82 | 5,100 | 2,100 | 2.40 |
| 13 | 4 | Cl | c-C$_6$H$_{10}$ | THF | 112 | 81 | 5,300 | 2,350 | 2.25 |
| 14 | 4 | Cl | c-C$_6$H$_{10}$ | hexane/CH$_2$Cl$_2$, 2:1 | 144 | 81 | 2,800 | 1,300 | 2.15 |
| 15 | 4 | Cl | c-C$_6$H$_{10}$ | ether/CH$_2$Cl$_2$, 2.5:1 | 96 | 84 | 4,900 | 3,200 | 1.53 |

*Estimated by GPC

The enzyme-catalyzed polymerization method according to the present invention is advantageous in several respects. The polymerization reactions are effected at ambient temperature or slightly above. This allows reactive functional groups, for example, epoxide groups, to be present in the monomers, which groups would probably not survive normal polycondensation conditions required for polyester production. Additionally, the stereo- and regioselectivity of the enzyme which is employed as catalysts permits the construction of polymers having highly regular structures. Additionally, the present method may be employed to produce polymers having a very narrow, and, perhaps easily controlled, molecular weight distribution.

The preceding examples are set forth to illustrate specific embodiments of the invention and are not intended to limit the scope of the compositions and methods of the present invention. Additional embodiments and advantages within the scope of the claimed invention will be apparent to one of ordinary skill in the art.

What is claimed is:

1. A method for synthesizing a polyester, comprising reacting a diester and a dialcohol at approximately ambient temperature in the presence of a hydrolase enzyme catalyst, said diester and said dialcohol being reacted in a molar ratio of about 2:1 when said diester is of racemic character and in equimolar amounts when said diester is of nonracemic character, and said polyester exhibiting a weight average molecular weight, Mw, as measured by gel permeation chromatography, of at least about 3000.

2. A method for enantioselectively polymerizing a diester and a dialcohol to form a polyester, comprising reacting the diester and the dialcohol at approximately ambient temperature in the presence of a hydrolase enzyme catalyst, said diester and said dialcohol being reacted in a molar ratio of about 2:1 when said diester is of racemic character and in equimolar amounts when said diester is of nonracemic character, and said polyester exhibiting a weight average molecular weight, Mw, as measured by gel permeation chromatography, of at least about 3000.

3. A method as defined by either of claims 1 or 2, wherein the enzyme catalyst comprises a lipase.

4. A method as defined by claim 3, wherein the enzyme catalyst comprises porcine pancreatic lipase.

5. A method as defined by either of claims 1 or 2, wherein the diester is a bis-substituted alkanedioate of the formula

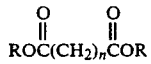

wherein n is from 2 to about 10, and R is selected from alkyl, halogen-substituted alkyl, alkenyl, aryl, substituted aryl and aroyl groups.

6. A method as defined by claim 5, wherein R is selected from alkyl, halogen-substituted alkyl, vinyl, 2-propenyl, phenyl, nitrophenyl, monohalogen-substituted phenyl, polyhalogen-substituted phenyl, cyanophenyl and benzoyl groups.

7. A method as defined by claim 5, wherein the diester is of the formula

wherein Y is Cl or F and n is from 2 to about 10.

8. A method as defined by claim 5, wherein n is 3 or 4.

9. A method as defined by either of claims 1 or 2, wherein the diester comprises bis(2,2,2-trichloroethyl) (±)-3,4-epoxyadipate.

10. A method as defined by either of claims 1 or 2, wherein the dialcohol is of the formula

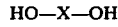

wherein X comprises a hydrocarbon group containing from about 4 to about 15 carbon atoms.

11. A method as defined by claim 10, wherein the dialcohol is of the formula

HOCH₂—Z—CH₂OH wherein Z comprises a hydrocarbon group containing from about 2 to about 10 carbon atoms.

12. A method as defined by claim 11, wherein the diol is selected from 1,4-butanediol, 1,6-hexanediol, 1,12-dodecanediol and 1,4-cyclohexane dimethanol.

13. A method as defined by either of claims 1 or 2, wherein the reaction is conducted in the presence of an organic solvent.

14. A method as defined by claim 13, wherein the organic solvent is of low to intermediate polarity.

15. A method as defined by claim 13, wherein the organic solvent is selected from hexane, diethyl ether, diisopropyl ether, dipropyl ether, tetrahydrofuran, benzene, 1,1,2-trichlorotrifluoromethane, chloroform, o-dichlorobenzene, and mixtures of methylene chloride with hexane or ether.

16. A method of synthesizing an optically active polyester, comprising enantioselectively polymerizing bis(R)(±)-3,4-epoxyadipate in which R is selected from phenyl, 4-nitrophenyl, 4-chlorophenyl, 4-fluorophenyl, 4-bromophenyl and 2,4-dichlorophenyl, with a dialcohol selected from 1,4-butanediol, 1,6-hexanediol and 1,6-cyclohexanedimethanol in a molar ratio of 2:1 at approximately ambient temperature in the presence of an enzyme catalyst comprising a lipase.

17. A method of synthesizing an optically active polyester, comprising enantioselectively polymerizing a diester selected from bis(2,2,2-trifluoroethyl) (±)-3,4-epoxyadipate and bis(2,2,2-trichloroethyl) (±)-3,4-epoxyadipate, with 1,4-butanediol in a molar ratio of 2:1 at approximately ambient temperature in the presence of an enzyme catalyst comprising porcine pancreatic lipase.

18. A method for synthesizing a polyester, comprising reacting a diester and a dialcohol at approximately ambient temperature in the presence of a hydrolase enzyme catalyst, said diester and said dialcohol being reacted in a molar ratio of about 2:1 when said diester is of racemic character and in equimolar amounts when said diester is of nonracemic character, and said polyester exhibiting a weight average molecular weight, Mw, as measured by gel permeation chromatography, of at least 3000, wherein said diester comprises a bis-substituted alkanedioate of the formula $$\text{ROC(CH}_2)_n\text{COR}$$
$$\overset{O}{\underset{\|}{\phantom{R}}}\phantom{OC(CH_2)_n}\overset{O}{\underset{\|}{\phantom{R}}}$$

wherein n is from 2 to about 10, and R is selected from alkyl, halogen-substituted alkyl, alkenyl, aryl and substituted aryl groups, and said dialcohol is of the formula

HO—X—OH wherein X comprises a hydrocarbon group containing from about 4 to about 15 carbon atoms.

19. A method for enantioselectively polymerizing a diester and a dialcohol to form a polyester, comprising reacting the diester and the dialcohol at approximately ambient temperature in the presence of a hydrolase enzyme catalyst, said diester and said dialcohol being reacted in a molar ratio of about 2:1 when said diester is of racemic character and in equimolar amounts when said diester is of nonracemic character, and said polyester exhibiting a weight average molecular weight, Mw, as measured by gel permeation chromatography, of at least about 3,000, wherein said diester comprises an alkanedioate of the formula $$\text{ROC(CH}_2)_n\text{COR}$$

wherein n is from 2 to about 10, and R is selected from alkyl, halogen-substituted alkyl, alkenyl, aryl and substituted aryl groups, and said dialcohol is of the formula

HO—X—OH wherein X comprises a hydrocarbon group containing from about 4 to about 15 carbon atoms.

* * * * *